United States Patent
Yadav et al.

[11] Patent Number: 6,093,830
[45] Date of Patent: Jul. 25, 2000

[54] ENANTIOSELECTIVE RESOLUTION PROCESS FOR ARYLPROPIONIC ACID DRUGS FROM THE RACEMIC MIXTURE

[75] Inventors: Nirmal Kishor Yadav; Bhaskar Dattatraya Kulkarni; Ramdas Bhagvan Khomane, all of Maharashtra, India

[73] Assignee: Council of Scientific and Industrial Research, India

[21] Appl. No.: 09/268,554

[22] Filed: Mar. 15, 1999

[30] Foreign Application Priority Data

Nov. 9, 1998 [IN] India ............... 3317/DEL/98

[51] Int. Cl.⁷ .................................... C07B 57/00
[52] U.S. Cl. .................. 548/217; 562/401; 562/466; 562/492; 562/494
[58] Field of Search ................ 562/401, 466, 562/492, 494; 548/217

[56] References Cited

U.S. PATENT DOCUMENTS

| | | |
|---|---|---|
| 4,209,638 | 6/1980 | Nicholson et al. . |
| 4,246,164 | 1/1981 | Felder et al. . |
| 4,246,193 | 1/1981 | Holton . |
| 4,501,727 | 2/1985 | Armitage et al. . |
| 4,515,811 | 5/1985 | Holton . |
| 4,983,765 | 1/1991 | Lukas et al. . |
| 4,994,604 | 2/1991 | Tung et al. . |
| 5,015,764 | 5/1991 | Manimaran et al. . |
| 5,189,208 | 2/1993 | Stahly . |
| 5,332,834 | 7/1994 | Bhattacharya et al. . |
| 5,599,969 | 2/1997 | Hardy et al. . |
| 5,621,140 | 4/1997 | Schloemer et al. . |
| 5,852,209 | 12/1998 | Nohira et al. . |

*Primary Examiner*—Gary Geist
*Assistant Examiner*—Leigh C. Maier
*Attorney, Agent, or Firm*—Jenkens & Gilchrist

[57] ABSTRACT

The invention relates to a novel non-catalytic enantioselective resolution process for the separation of enantiomer of arylpropionic acid drugs from the racemic mixture, which comprises dissolving the racemic mixture of the said drug an organic solvent, reacting this solution with an aqueous phase containing an ionic surfactant with or without a suitable co-surfactant, and an electrolyte in microemulsion/micellar/biphasic medium, reacting this mixture with an appropriate chiral amine at a temperature in the range of 0 to 70 degrees Celsius to obtain a diastereomeric salt, acid hydrolysing the diastereomeric salt to result in the pure enantiomer of the drug which is extracted by known methods.

23 Claims, No Drawings

ENANTIOSELECTIVE RESOLUTION PROCESS FOR ARYLPROPIONIC ACID DRUGS FROM THE RACEMIC MIXTURE

FIELD OF THE INVENTION

The invention relates to a new enantioselective resolution process for the separation of arylpropionic acid drugs from the racemic mixture.

BACKGROUND OF THE INVENTION

The main industrial method for preparation of pure enantiomers constitutes the resolution of racemates. The present invention relates to the production of pure enantiomer of arylpropionic acid selected from profen family of drugs such as ibuprofen, flurbiprofen, flunoxaprofen, naproxen etc. The methods for such resolution include: direct preferential crystallization, crystallization of the distereomeric salts, kinetic resolution, enzymatic resolution, differential absorption and asymmetric synthesis.

The Industrial processes for production of drugs such as Amoxycillin, Ampicillin, Captropril, Diltiazem, Naproxen, Cefalexin, Cefadroxil, Timolol, α-methyl L-dopa, chloramphenicol, Dextromethorphan and Ethambutol etc. use racemate resolution via crystallization. Technical feasibility of such processes is restricted to conglomerates which are less than 20% of all racemates. In case of true racemic compounds, the seeding of one enantiomer does not separate the other enantiomer by preferential crystallization.

The conglomerate exhibits a minimum melting point for the racemic mixture while a racemic compound shows a maximum melting point. The success of preferential crystallization depends on the fact that the two enantiomers crystallize at different rates and on the correlation between the melting point diagram and the solubility phase diagram, i.e., the mixture having the lowest melting point is the most soluble, and for a conglomerate this is the racemic mixture. Ibuprofen is a true racemic compound.

If the true racemic compound is a homogeneous solid phase of two enantiomers co-existing in the same unit cell, it may be separated by diastereomer crystallization, this generally involves a reaction of the racemate with an optically pure acid or base (the resolving agent) to form a mixture of diastereomeric salts which is separated by crystallization.

Diastereomeric crystallization is widely used on Industrial scale. A typical example is production of D(-)Phenyl glycine, an antibiotic intermediate, using camphor sulphonic acid as a resolving agent. There are natural and semisynthetic resolving agents such as Tartaric acid, Maleic acid, Camphor sulphonic acid, Mandelic acid, Phenoxy propionic acid, hydratopic acid, Brucine, Quinine, Ephedrine, α-Methylbenzylamine, Amphetamine, Deoxyehedrine, and N-Methyl D-Glucamine etc.

The theoretical once-through yield of a resolution via diastereomer crystallization is 50 percent. However, in practice, a single re-crystallization produces a composition that is simply an enantiomerically enriched racemate. This means that the innovation, if any, may come at this particular stage of unit process/operation.

Another method for the resolution of racemates is the kinetic resolution, the success of which depends on the fact that the two enantiomers react at different rates with a chiral addend. The industrial process such as production of S-Naproxen by CCL-catalyzed and enzymatic hydrolysis of the methyl ester, was reported by Sih and Coworkers (Sih, C. J., Gu, Q. M. Fulling, G., Wu, S. H. and Reddy, D. R., Dev. Ind. Microbiol., 29, 221–229(1988), Gu, Q. M., Chen, C. S., and Shih, C. J., Tetrahedron Lett, 27, 1763(1986)).

The enantioselective conversion of a prochiral substrate to an optically active product, by reaction with a chiral addend, is referred to as an asymmetric synthesis. The manufacture of L-Dopa by Monsanto is a typical industrial example. See Knowles, et. Al., J. Am. Chem. Soc., 97, 2567(1975).

With the exception of the preferential crystallization process, when applied to Ibuprofen, the prior art processes typically produce a first mixture that is essentially an enantiomerically enriched racemic composition. A number of crystallizations are required to yield the pure enantiomer.

Numerous processes for the preparation of S(+)-Ibuprofen have been disclosed, most relate to resolution.

The use of S(-)-α-methylbenzylamine as the resolving agent has been described in the patent and non-patent literature. Kaiser et. al., J. Pharm. Sci., 65(2), 269–274 (1976), discloses the separation of (S)-Ibuprofen from racemic Ibuprofen. U.S. Pat. No. 4,209,638 (Nicholson et. al.) discloses a process for increasing the proportion of desired enantiomer from racemic phenyl propionic acid (such as Ibuprofen) by a partial dissolution technique. U.S. Pat. No. 4,983,765, (Lukas et. Al.) discloses a separation process in which the reaction to a diasteriomeric salt takes place in a polar solvent, and the salt is purified by several crystallizations to produce optically pure material U.S. Pat. No. 5,015,764 (Manimaran et. al.) discloses a process in which the racemic mixture is initially treated with an organic or inorganic base to form a salt solution, and the salt solution is treated with a chiral base such as (S)-α-methylbenzylamine to precipitate the less soluble diastereomeric salt from the reaction solution, and PCT Published Application No. WO 93/15040 (Ethyl Corporation) discloses an invention wherein an inorganic or organic salt soluble in the solution of the resolution process, is added to enhance the separation. The process discloses the use of an inert organic or an inorganic salt such as triethylamine, preferably an alkali metal, alkaline earth metal or ammonium salt, most preferably sodium, potassium or ammonium salts of halides (fluoro, chloro, bromo or iodo salts) to enhance separation of less soluble diastereomer from mixture. Nitrates and acetate salts are also useful in the process of the above application Especially preferred is sodium chloride. It can be added at different stages of the process to improve separation of less soluble diastereomer.

U.S. Pat. No. 4,994,604 (Tung et. al.) discloses the use of (S)-lysine in a preferential crystallization method for the formation of the (S)-Ibuprofen(S)-lysine salt; and U.S. Pat. No. 5,332,834 (Bhattacharya et. al.) discloses an improvement on that process including the racemization and recycle of (R)-Ibuprofen. European Patent No. 0529835 (Nagase & Co.) discloses the use of various optically active phenyl substituted amines, such as 2-(4-methylphenyl)-3-methylbutylamine, as resolving agents.

U.S. Pat. No. 4,246,164 (Felder et. al.) discloses the use of N-methyl-D-glucamine and U.S. Pat. Nos. 4,246,193 and 4,515,811 (Holten) disclose the use of other N-alkyl-D-glucamines as resolving agents in the preparation of Naproxen.

U.S. Pat. No. 4,501,727 (Armitage et. al.) discloses N-methyl-D-glucamine salt of (+)-flurbiprofen although it does not disclose it as a resolving agent.

U.S. Pat. No. 5,621,140 (George et. al.) discloses a Ibuprofen resolution process using N-methyl-D-glucamine [6284-40-8] and N-octyl-D-glucamine. The S-Ibuprofen yield is 73.2% and 74% and ee is 99% and 99.9% respectively.

U.S. Pat. No. 5,599,969 (Robert Hardy et. al.) discloses a process of Ibuprofen resolution using (S)-α-methylbenzylamine. The process produces S-Ibuprofen of 89.3% purity (by weight). It discloses resolution methods for phenyl propionic acid in general covering Ibuprofen, flurbiprofen and their pharmaceutically acceptable salts.

U.S. Pat. No. 5,189,208 (G. Patrick Stably and Baton Rouge, La.) discloses an Ibuprofen resolution process using a non racemic Ibuprofen as its starting material obtained from an enantioselective synthesis process.
The enantiomeric excess is enriched by removing close to racemic composition as crystals leaving behind an enriched S-enantiomer of Ibuprofen in mother liquor.

In another pending Indian Patent Application No. 286DEL/95 filed in 1995 by N. K. Yadav and B. D. Kulkarni filed for Enantioselective separation of chiral drugs, the application of surfactant and co-surfactant along with some deemulsifying agent, such as NaCl, produces optical/activity of organic aqueous phases indicating that the system can be used for enantioselective separation of chiral drugs into enantiomers.

OBJECTS OF THE INVENTION

The objective of the present invention is to provide new non-catalystic process for the enantioselective resolution of pure enantiomer from racemic arylpropionic acids.

It is a further object of the present invention to obtain such pure enantiomer from compositions of enantiomerically enriched racemic arylpropionic acids in a continuous process.

It is a further object of the present invention to improve upon the earlier processes by improving upon the single pass enantioselectivity of diastereomerization of arylpropionic acids as S(+)-arylpropionic acid S-(-)-amine salt.

DETAILED DESCRIPTION OF THE INVENTION

Accordingly, the present invention provides a new enantioselective resolution process for separation of enantiomer of arylpropionic acid drugs from the racemic mixture which comprises dissolving the racemic mixture of the drug in a suitable organic solvent, reacting this solution with an aqueous phase containing an ionic surfactant with or without suitable co-surfactant and an electrolyte in microemulsion/micellar/biphasic medium, reacting this mixture with an appropriate chiral amine at a temperature in the range of 0 to 70 degree Celsius to obtain a diastereomeric salt, acid hydrolysing the diastereomeric salt to obtain the pure enantiomer of the drug by known method.

In one embodiment the arylpropionic acid drug may be selected from Ibuprofen, flurbiprofen, Flunoxaprofen, Naproxen and, preferably Ibuprofen.

In one of the embodiments of the present invention, the organic solvent for dissolving the drug may be selected from hydrocarbon, cyclic hydrocarbon, aromatic compounds, aromatic with alkyl side chain, solvents with ether group, and solvents with keto group preferably cyclohexane.

In another embodiment the surfactants used may be sodium dodecyl sulfate (SDS), dodecyl benzene sulfonic acid sodium salt (SDBS) or cationic surfactant i.e. cetyl trimethyl ammonium bromide (CTAB) or commercially available Span (sorbiton esters) and Tween (polyoxyethylene-sorbiton esters) series surfactants, preferably sodium dodecyl sulfate (SDS) in the concentration range 1 cmc to 100 cmc, more preferably 1 to 20 cmc.

In another embodiment, the optional co-surfactant may be chosen from a long chain alkanol, preferably pentanol.

In another embodiment, an electrolyte may be chosen from a mono, di, or tri valent metal ion with halide as anion, preferably mono valent metal ion with halide as anion such as NaCl in the concentration range 1 mili moles per liter to 1 mole per liter, more preferably 0.05 moles per liter to 0.5 moles per liter.

In another embodiment, the chiral reagent may be chosen from a list of optically active compounds with an amine group attached to an alkyl chain, cyclic chain, phenyl ring, glucose ring or chain, preferably α-methylbenzylamine in the molar ratio of arylpropionic acid chiral amine ranging from 1:0.25 to 1:1, more preferably in the range of 1:0.4 to 1:0.6.

In another embodiment, the acids used may be a mineral acid, preferably sulfuric acid in the concentration range 0.1 N to 5 N, preferably 0.5 N to 3 Normal.

In another embodiment, the leaching organic solvent may be selected from aliphatic hydrocarbons i.e., hexane, heptane, octane, etc., aromatic hydrocarbon solvents, i.e., benzene, toluene, xylene and cyclic hydrocarbon i.e., cyclohexane etc. and solvents such as ether or acetone, preferably ether may be used.

The present invention is described in the following examples, which are illustrative only and should not however considered to limit the scope of the present invention in any manner whatsoever.

EXAMPLE-1

1.5032 grams of racemic Ibuprofen is dissolved in 30 grams of cyclohexane. 0.04538 grams of Sodium dodecyl benzene, sulfonate is dissolved in 30.0 grams of distilled water. Both the organic and aqueous phases are mixed together and stirred well. To this mixture, 0.8 grams of Sodium chloride is added and the mixture is stirred and then 0.44925 grams of S(-)-α-methylbenzylamine is added at room temperature to the above mixture and stirred. The reaction product is filtered after an hour and the product is washed with distilled water to remove unreacted impurities. The product diastereomer is acid hydrolyzed using 3 Normal Sulfuric acid and extracted with diethyl ether.

The HPLC analysis of solution with Chiralcel OD Column along with a guard column containing S(+)-Ibuprofen showed 59.71% by weight and enantiomeric excess was 21.79%.

EXAMPLE-2

1.5 gm of racemic ibuprofen is dissolved in 30 gm of cyclohexane. To this solution, 0.14304 gm of sodium dodecyl sulfate (SDS) in 30 gm of distilled water is added. To this biphasic system, 0.177 gm of sodium chloride (NaCl) is added. This solution is cooled in an ice bath, and to this ice cooled solution with proper shaking, 0.44 gm of S-(-)α-methylbenzylamine is added dropwise, which results into precipitation of diastereomeric. Thus diastereomeric salt was filtered and washed 2–3 times using ice cooled distilled water and dried at room temperature. The weight of diastereomeric product was 0.8 gm.

0.5 gm of diastereomeric salt is acid hydrolyzed in 60 ml 1.5 N $H_2SO_4$ and this solution was stirred using a magnetic needle on a magnetic stirrer. This solution was poured in a separating funnel and it was extracted with 50 ml diethyl ether in two batches. Diethyl ether was evaporated, yield of enantiomer was 0.305 gm.

The HPLC analysis of solution using Chiralcel OD Column along with a guard column containing S(+)-Ibuprofen showed 54.12% by weight and the enantiomeric excess of S-(+)-Ibuprofen was 23.42%.

EXAMPLE-3

0.3 gms of naproxen with about 56.7% enantiomeric excess (ee) of s-naproxen is dissolved in 20 gms of cyclohexane. 0.09469 gms of SDS is dissolved in 20 gms of distilled water. Both the phases are mixed and stirred well. 0.234 gms of NaCl is added to the above solution and the mixture is stirred.

0.079 gms of s(−)-α-methylbenzylamine is added under stirring and the mixture is stirred for half an hour at room temperature. The product is cooled by ice cooled water.

0.05025 gms of diastereomer salt obtained by above process is acid hydrolyzed using 1N $H_2SO_4$ and the product is extracted with diethyl ether. The product is analysed by chiral HPLC indicated 78.81% ee of s-naproxen, a 20.11% enrichment of s-naproxen over the starting material of naproxen.

The advantages of the present invention are:
1. the present invention provides an improvement in single pass enantioselectivity of desired enantiomer over the earlier processes which are limited to 50% conversion per pass. The novelty of the present invention lies in achieving enantioselective diastereomerization without using chiral selective catalyst in a microemulsion/micellar/biphasic medium. The desired enantiomer of arylpropionic acid drug from racemic or enriched racemic mixture to the desired diastereomeric salt of S(+)-arylpropionic acid and S(−)-Amine is obtained without using a chiral catalyst.
2. The present invention provides a continuous enantioselective resolution process for arylpropionic acid drugs using racemic or enriched racemic mixture of acid drugs.

The invention provides an economical way of achieving an enantioselective resolution of arylpropionic acid drug as compared with an enantioselective catalytic process.

The invention can be easily implemented to produce enantioselective pure drugs from racemic or enriched racemic mixture of arylpropionic acid drugs for existing process plants of such drugs.

What is claimed is:

1. A non-catalytic enantioselective resolution process for the separation of a preferred enantiomer of arylpropionic acid drug from the racemic mixture, which comprises dissolving the racemic mixture of the drug in an organic solvent to form a solution, reacting the solution with an aqueous phase containing an ionic surfactant with an optional suitable co-surfactant, and an electrolyte in a biphasic medium to form a mixture, reacting the mixture with an appropriate chiral reagent at a temperature in the range from 0 to 70 degrees Celsius to obtain a diastereomeric salt, and acid hydrolysing the diastereomeric salt to result in the preferred enantiomer of the drug which is extracted by known methods.

2. The process of claim 1, wherein the arylpropionic acid drug is selected from the group consisting of Ibuprofen, Flurbiprofen, Flunoxaprofen, and Naproxen.

3. The process of claim 2, wherein the arylpropionic acid drug is Ibuprofen.

4. The process of claim 1, wherein the organic solvent used for dissolving the racemic mixture of the drug is selected from hydrocarbons, cyclic hydrocarbons, aromatic compounds, aromatic hydrocarbons with alkyl side chains, solvents with ether group and solvents with keto group.

5. The process of claim 4, wherein the organic solvent is cyclohexane.

6. The process of claim 1 wherein the ionic surfactant is a cationic surfactant selected from the group consisting of cetyl trimethyl ammonium bromide (CTAB), sorbiton esters and polyoxyethylene-sorbiton esters.

7. The process of claim 6, wherein the cationic surfactant is sodium dodecyl sulfate (SDS).

8. The process of claim 1 wherein the concentration of the sodium dodecylsulfate is in the range of from 1–20 cmc.

9. The process of claim 1, wherein the ionic surfactant includes the optional co-surfactant, the optional co-surfactant is chosen from alkanols with a carbon chain length greater than 4.

10. The process of claim 9, wherein the alkanol is pentanol.

11. The process of claim 1, wherein the electrolyte is selected from a mono, di or trivalent metal ion with halide as anion.

12. The process of claim 11, wherein the electrolyte is a monovalent metal ion with halide as anion is NaCl.

13. The process of claim 1, wherein the concentration of the electrolyte may be in the range of 1 mmol/liter to 1 mole per liter.

14. The process of claim 13, wherein the concentration of the electrolyte is from 0.05 moles/liter to 0.5 moles liter.

15. The process of claim 1, wherein the chiral reagent is selected from the group of optically active with amine group attached to an alkyl chain, a cyclic chain, a phenyl ring, a glucose ring or a glucose chain.

16. The process of claim 15, wherein the chiral reagent is methylbenzylamine.

17. The process of claim 1, wherein the molar ratio of arylpropionic acid: chiral reagent is in the range of from 1:0.25 to 1:1.

18. The process of claim 17, wherein the molar ratio of arylpropionic acid: chiral reagent is in the range of from 1:0.4 to 1:0.6.

19. The process of claim 1, wherein the arylpropionic acid is a mineral acid with a concentration in the range from 0.1N to 5N.

20. The process of claim 1, wherein the arylpropionic acid is sulfuric acid.

21. The process of claim 19, wherein the concentration of the arylpropionic acid is in the range of from 0.5N to 3N.

22. The process of claim 1, wherein the preferred enantiomer is extracted by an organic solvent selected from the group consisting of aliphatic hydrocarbons, aromatic hydrocarbons, ether, acetone, hexane, heptane, octane, benzene, toluene, xylene, and cyclohexane.

23. The process of claim 22, wherein the extraction solvent is ether.

* * * * *